United States Patent
Baldauf et al.

(10) Patent No.: US 9,255,321 B2
(45) Date of Patent: Feb. 9, 2016

(54) DIRECTED SURFACE FUNCTIONALIZATION ON SELECTED SURFACE AREAS OF TOPOGRAPHICAL FEATURES WITH NANOMETER RESOLUTION

(71) Applicant: International Business Machines Corporation, Armonk, NY (US)

(72) Inventors: Julia Baldauf, South Melbourne (AU); Stefan Harrer, Hampton (AU); Christine Schieber, Southbank (AU)

(73) Assignee: GLOBALFOUNDRIES INC., Grand Cayman (KY)

( * ) Notice: Subject to any disclaimer, the term of this patent is extended or adjusted under 35 U.S.C. 154(b) by 33 days.

(21) Appl. No.: 14/053,972

(22) Filed: Oct. 15, 2013

(65) Prior Publication Data
US 2015/0104353 A1    Apr. 16, 2015

(51) Int. Cl.
| | |
|---|---|
| *G01N 33/53* | (2006.01) |
| *C23C 14/12* | (2006.01) |
| *C23C 14/22* | (2006.01) |
| *C23C 14/34* | (2006.01) |
| *G01N 33/487* | (2006.01) |
| *G01N 33/543* | (2006.01) |
| *G01N 33/553* | (2006.01) |
| *C23C 14/04* | (2006.01) |
| *G01N 33/551* | (2006.01) |
| *G01N 33/533* | (2006.01) |
| *B82Y 5/00* | (2011.01) |
| *B82Y 15/00* | (2011.01) |

(52) U.S. Cl.
CPC ............ *C23C 14/12* (2013.01); *C23C 14/046* (2013.01); *C23C 14/22* (2013.01); *C23C 14/221* (2013.01); *C23C 14/225* (2013.01); *C23C 14/34* (2013.01); *G01N 33/48721* (2013.01); *G01N 33/54373* (2013.01); *G01N 33/553* (2013.01); *B82Y 5/00* (2013.01); *B82Y 15/00* (2013.01); *G01N 33/533* (2013.01); *G01N 33/551* (2013.01)

(58) Field of Classification Search
None
See application file for complete search history.

(56) References Cited

U.S. PATENT DOCUMENTS

| | | |
|---|---|---|
| 5,397,695 A | 3/1995 | Sutton et al. |
| 6,428,959 B1 | 8/2002 | Deamer |
| 6,627,067 B1 | 9/2003 | Branton et al. |
| 7,625,469 B1 | 12/2009 | Yelton et al. |
| 7,846,656 B2 | 12/2010 | Mirzabekov et al. |

(Continued)

FOREIGN PATENT DOCUMENTS

WO      0127610 A3    4/2001

OTHER PUBLICATIONS

International Search Report and Written Opinion dated Jan. 22, 2015 for Application No. PCT/US2014/50644.

(Continued)

*Primary Examiner* — Jill Warden
*Assistant Examiner* — Timothy G Kingan
(74) *Attorney, Agent, or Firm* — Cantor Colburn LLP

(57) ABSTRACT

A method for making a single molecule receptor in a nanopore structure includes depositing a material by a physical vapor deposition (PVD) technique onto a selected interior surface of a nanochannel and functionalizing a surface of the material with a chemical compound having at least two functional groups. The material forms a patch having a diameter of about 3 to about 10,000 nanometers (nm). Also disclosed are embodiments of a nanopore structure including a single molecule receptor.

7 Claims, 5 Drawing Sheets

(56) References Cited

U.S. PATENT DOCUMENTS

| | | | |
|---|---|---|---|
| 8,105,471 | B1 | 1/2012 | Han et al. |
| 8,232,105 | B1 | 7/2012 | Scott |
| 8,247,238 | B2 | 8/2012 | Meinhart et al. |
| 8,262,879 | B2 | 9/2012 | Oliver |
| 8,278,055 | B2 | 10/2012 | Su et al. |
| 8,388,908 | B2 | 3/2013 | Blaga et al. |
| 8,481,334 | B1 | 7/2013 | Saul |
| 8,906,609 | B1 | 12/2014 | Smirnov et al. |
| 2003/0040173 | A1 | 2/2003 | Fonash et al. |
| 2004/0202994 | A1 | 10/2004 | Timperman |
| 2005/0221333 | A1 | 10/2005 | Sundararajan et al. |
| 2006/0019247 | A1 | 1/2006 | Su et al. |
| 2006/0231419 | A1* | 10/2006 | Barth et al. .................. 205/775 |
| 2006/0275778 | A1 | 12/2006 | Wu et al. |
| 2007/0138132 | A1 | 6/2007 | Barth |
| 2008/0003571 | A1 | 1/2008 | McKernan et al. |
| 2008/0067056 | A1 | 3/2008 | Searson et al. |
| 2008/0073512 | A1 | 3/2008 | Siuzdak et al. |
| 2009/0136948 | A1 | 5/2009 | Han et al. |
| 2009/0305273 | A1 | 12/2009 | Cao et al. |
| 2010/0009872 | A1 | 1/2010 | Eid et al. |
| 2010/0151454 | A1* | 6/2010 | Sundararajan et al. ........... 435/6 |
| 2011/0053284 | A1 | 3/2011 | Meller et al. |
| 2011/0168562 | A1 | 7/2011 | Nuckolls et al. |
| 2012/0088315 | A1 | 4/2012 | Merelle et al. |
| 2012/0193231 | A1 | 8/2012 | Afzali-Ardakani et al. |
| 2012/0222958 | A1 | 9/2012 | Pourmand et al. |
| 2012/0256281 | A1 | 10/2012 | Harrer et al. |
| 2013/0085680 | A1 | 4/2013 | Arlen et al. |
| 2013/0256137 | A1* | 10/2013 | Holt .............................. 204/601 |
| 2014/0045270 | A1 | 2/2014 | Shim et al. |
| 2014/0106472 | A1 | 4/2014 | Ervin et al. |
| 2014/0206101 | A1* | 7/2014 | Liu et al. ....................... 436/501 |

OTHER PUBLICATIONS

Liu, Changlu, et al.; "Relaxin-3/Insulin-Like Peptide 5 Chimeric Peptide, a Selective Ligand for G Protein-Coupled Receptor (GPCR)135 and GPCR142 over Leucine-Rich Repeat-Containing G Protein-Coupled Receptor 7"; Molecular Pharmacology; vol. 67, No. 1; p. 231-240; 2005.
Danelon, Christophe, et al.; "Fabrication and Functionalization of Nanochannels by Electron-Beam-Induced Silicon Oxide Deposition"; Langmuir; vol. 22; p. 10711-10715; 2006.
Hou, Xu, et al.; "Building Bio-Inspired Artificial Functional Nanochannels: From Symmetric to Asymmetric Modification"; Angew. Chem. Int. Ed.; vol. 51; p. 5296-5307; 2012.
International Search Report and Written Opinion dated Dec. 18, 2014 for Application No. PCT/US2014/052481.
International Search Report and Written Opinion dated Dec. 29, 2014 for Application No. PCT/US2014/058531.
I. Braslavsky, et al., "Sequence Information Can Be Obtained From Single DNA Molecules," Department of Applied Physics, California Institute of Technology; PNAS Apr. 1, 2003; vol. 100; No. 7; pp. 3960-3964.
D. Branton, et al., "The Potential and Challenges of Nanopore Sequencing," Nature Biotechnology; 2008 Nature Publishing Group; pp. 1146-1153.
F. Collins, et al., "The Human Genome Project: Lessons from Large-Scale Biology," Apr. 11, 2003 vol. 300 Science www.sciencemag.org; pp. 286-290.
M. Fedurco, et al., "BTA, a Novel Reagent for DNA Attachment on Glass and Efficient Generation of Solid-Phase Amplified DNA Colonies," Nucleic Acids Research, 2006, vol. 34, No. 3; Published online Feb. 9, 2006; pp. 1-13.
S. Harrer, et al., "Electrochemical Characterization of Thin Film Electrodes Toward Developing a DNA Transistor," Langmuir Article 2010 American Chemical Society; Langmuir 2010, 26(24), pp. 19191-19198.
T. Harris, et al., "Single-Molecule DNA Sequencing of a Viral Genome," Science vol. 320, 106 (2008); pp. 106-109.
J. Kasianowicz, et al., "Characterization of Individual Polynucleotide Molecules Using a Membrane Channel," Proc. Natl. Acad. Sci. USA; vol. 93; pp. 13770-13773; Nov. 1996 Biophysics.
B. Luan, et al., "Tribological Effects on DNA Translocation in a Nanochannel Coated with a Self-Assembled Monolayer," J. Phys. Chem B., 2010, 114, pp. 17172-17176.
B. Luan, et al., "Base-by-Base Ratcheting of Single Stranded DNA Through a Solid-State Nanopore," Physical Review Letters 104, 238103 (2010); pp. 238103-1-238103-4.
B. Luan, et al., "Control and Reversal of the Electrophoretic Force on DNA in a Charged Nanopore," J. Phys.: Condens. Matter 22 (2010) 454123 (5pp).
M. Margulies, et al., "Genome Sequencing in Microfabricated High-Density Picolitre Reactors," Nature vol. 437; Sep. 15, 2005 pp. 376-380.
S. Polonsky, et al., "Nanopore in Metal-Dielectric Sandwich for DNA Position Control," Applied Physics Letters 91, 153103 (2007); pp. 153103-1-153103-3.
F. Sanger, et al., "DNA Sequencing with Chain-Terminating Inhibitors," Proc. Natl. Acad. Sci. USA; vol. 74, No. 12; pp. 5463-5467; Dec. 1977 Biochemistry.
D. Scott, et al., "Direct Molecular Evolution of Detergent-Stable G Protein-Coupled Using Polymers Encapsulated Cells," 2012 Elsevier Ltd., J. Mol. Biol. (2013) 425, pp. 662-677.
J. Shendure, et al., "Accurate Multiplex Polony Sequencing of an Evolved Bacterial Genome," Science 309, 1728 (2005); pp. 1728-1732.
G. Turcatti, et al., "A New Class of Cleavable Fluorescent Nucleotides: Synthesis and Optimization as Reversible Terminators for DNA Sequencing by Synthesis," Nucleic Acids Research, 2008, vol. 36, No. 4; Published online Feb. 7, 2008; pp. 1-13.
D. Wang, et al., "DNA-Translocation Through a Solid State Nanopore coated with a Functionally Switchable Self-Assembled Monolayer," IBM T. J. Watson Research Center, Yorktown Heights, NY USA; 2012; pp. 1-18.
D. Wang, et al., "Regulating the Transport of DNA through Biofriendly Nanochannels in a Thin Solid Membrane," IBM Research at T.J. Watson Center, Yorktown Heights, NY USA; pp. 1-23; Feb. 5, 2014.
E. Yusko, et al., "Developing Nanopores with Fluid Walls for Improved, Single-Molecule Biosensors," Abstract only Feb. 2012; 1 page.
Bayley, Hagan et al.; Stochastic Sensors Inspired by Biology; Nature; vol. 413; p. 226-230; Sep. 13, 2001.
Hickman, James J., et al.; "Toward Orthogonal Self-Assembly of Redox Active Molecules on Pt and Au: Selective Reaction of Disulfide with Au and Isocyanide with Pt"; Langmuir; vol. 8; 357-359; 1992.
Li, Zhiyong, et al.; "Self-Assembly of Alkanethiol Molecules onto Platinum and Platinum Oxide Surfaces"; Langmuir; vol. 19; p. 6744-6749; 2003.
Martin, Benjamin R., et al; "Orthogonal Self-Assembly on Colloidal Gold-Platinum Nanorods"; Advanced Materials; vol. 11, No. 12; p. 1021-1025; 1999.
Miles, Benjamin N., et al.; "Single Molecule Sensing with Solid-State Nanopores: Novel Materials, Methods, and Applications"; Chemical Society Reviews; vol. 42; No. 1; p. 15-28; Jan. 7, 2013.
Petrovykh, Dmitri Y., et al.; Alkanethiols on Platinum: Multicomponent Self-Assembled Monolayers; Langmuir; vol. 22; p. 2578-2587; 2006.
Raillon, C., et al.; "Fast and Automatic Processing of Multi-Level Events in Nanopore Translocation Experiments"; Nanoscale; vol. 4; p. 4916-4924; 2012.
Randolph, S. J., et al.; "Focused, Nanoscale Electron-Beam-Induced Deposition and Etching"; Critical Reviews in Solid State and Materials Sciences; vol. 31; p. 55-89; 2006.
Schoch et al., "Transport Phenomena in Nanofluidics," Reviews of Modern Physics, vol. 80, Jul.-Sep. 2008, 45 pages.
Tabard-Cossa, Vincent, et al.; "Noise Analysis and Reduction in Solid-State Nanopores"; Nanotechnology; vol. 18; p. 1-7; 2007.
Wei, Ruoshan, et al.; "Stochastic Sensing of Proteins with Receptor-Modified Solid-State Nanopores" Nature Nanotechnology; vol. 7; p. 257-263; Apr. 2012.
Harrer, S., et al., "Electrochemical Protection of Thin Film Electrodes in Solid State Nanopores," Nanotechnology 22 (2011) 275304 (6pp).

* cited by examiner

DIRECTED SURFACE FUNCTIONALIZATION ON SELECTED SURFACE AREAS OF TOPOGRAPHICAL FEATURES WITH NANOMETER RESOLUTION

BACKGROUND

The present invention relates to nanopores, and more specifically, to surface functionalized nanopores and functionalized nanochannels.

Solid-state nanopores and nanochannels of molecular dimensions can provide information on the chemical nature of analytes, e.g., deoxyribonucleic acid (DNA), proteins, and other biomolecules. Solid-state nanopore devices can include a multi-layer substrate having at least a single aperture, or "nanopore," which separates two salt solutions. The particular dimensions and compositions of nanopore devices are tailored to the desired application.

In operation, an electrical potential difference is generated across the nanopore by applying a voltage, and the ionic current passing through the nanopore is measured. Subsequently, passage of analytes through the nanopore induces interruptions in the measured open current level. A detected interruption, or ionic current drop, indicates passage of a single molecule of an analyte through the nanopore, which can also be referred to as a translocation event.

Translocation data can reveal properties about analytes traversing the pore on a single molecule level. Indirect measurement techniques, such as binding of the analyte to a receptor site inside the nanopore or nanochannel, can provide valuable information about the chemical and biological nature of many small chemical and biochemical compounds.

SUMMARY

According to one embodiment, a method for making a single molecule receptor in a nanopore structure comprises depositing a material by a physical vapor deposition (PVD) technique onto a selected interior surface of a nanochannel and functionalizing a surface of the material with a chemical compound having at least two functional groups. The material forms a patch having a diameter of about 1 to about 100 nanometers (nm).

In another embodiment, a method for making a single molecule receptor in a nanopore structure comprises tilting the nanopore structure at an angle with respect to a beam to position the beam onto a selected interior surface of a nanochannel in the nanopore structure, operating the beam to deposit the material onto a selected interior surface of the nanochannel, the material forms a patch having a surface area of about 3 to about 10,000 $nm^2$, and functionalizing a surface of the patch to form the single molecule receptor. The beam is operative to deposit a material by a PVD technique.

In yet another embodiment, a nanopore structure comprising a single molecule receptor comprises a substrate having a first surface and an opposing second surface, a nanochannel extending from the first surface to the opposing second surface and defining an interior surface, a material disposed on a selected area of the interior surface of the nanochannel, and a chemical compound disposed on the material to form a functionalized material. The material has a surface area of about 3 to about 10000 $nm^2$, and the functionalized material forms the single molecule receptor that binds to an analyte.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

Figure 1:
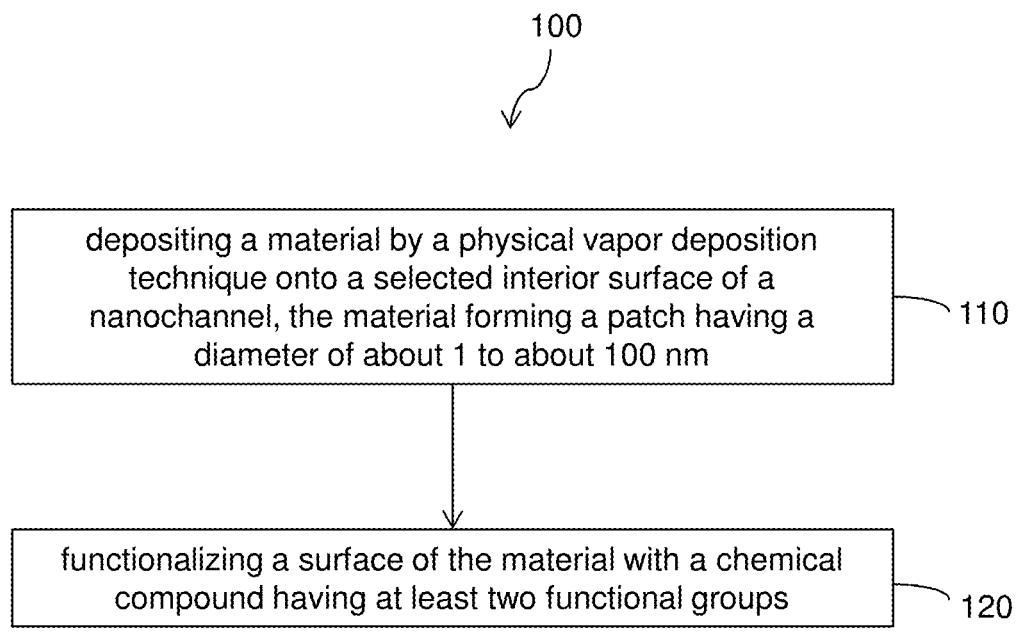
FIG. 1 illustrates a block diagram of an exemplary embodiment of a method for making a single molecule receptor in a nanopore structure.

Disclosed herein is a method for forming a single molecule receptor within a nanopore or a nanochannel. When a voltage is applied to a nanopore or nanochannel separating two ionic solutions, translocation and/or binding of a single molecule of an analyte induces a measurable change in ionic current. Accordingly, controlled translocation and/or reversible binding of a single molecule of an analyte, e.g., a protein or small biochemical compound, to a receptor in a nanopore can reveal physical and/or chemical properties of the analyte.

Providing a controlled embedded single binding site in a nanopore structure provides substantially higher reliability compared to systems in which multiple binding events can occur. The possibility of multiple binding events leads to more complicated data and subsequent interpretation. In contrast, the disclosed method provides a means to analyze a single binding event, which increases ease of data analysis, as well as reliability.

Furthermore, the method and nanopore structure disclosed provides for only two different translocation scenarios, one where binding to the single molecule binding site occurs and the other where binding does not occur. Again, such a scenario enables ease of data interpretation.

As used herein, the term "analyte" refers to a compound, molecule, substance, or chemical constituent that is undergoing analysis or sought to be detected. It is not intended that the present disclosure be limited to a particular analyte. Representative analytes include ions, saccharides, proteins, nucleic acids, and nucleic acid sequences.

As used herein, the term "single molecule receptor" refers to a structure to which a single molecule of a target component, or an analyte, binds or physically interacts. The single molecule receptor disclosed herein includes a functionalized material deposited onto an interior surface of a nanopore structure or nanochannel. A material forms a thin film or a patch having a size of nanometer dimensions, and the functionalized material includes a functional group, or an analyte binding group, that physically interacts with or binds to the analyte.

As used herein, the terms "nanopore" and "nanopore structure" refer to structures having solid substrate and a "nanochannel," or a nanoscale passageway through the substrate, through which ionic current can flow. The inner diameter of the nanopore or nanochannel can vary considerably depending on the intended use.

As used herein, the term "physical vapor deposition," "PVD," and the like refer to methods for deposition of thin films or coatings of a material onto a surface. These methods generally include condensation of a vaporized form of the material onto the surface. Non-limiting examples of PVD techniques include pulsed laser ablation, sputtering, electron-beam deposition, pulsed electron deposition, or any combination thereof. As used herein, the term "physical vapor deposition beam," "PVD beam," or "beam" refers to an ion beam or electron beam used in the PVD method.

As used herein, the term "functional group" encompasses atoms, combination of atoms, chemical groups, biochemical groups, biochemical molecules, or any combination thereof. The functional groups are any groups that can be directly linked or combined with a linker and which confer to the chemical compound described herein its chemical reactivity.

Figure 2:
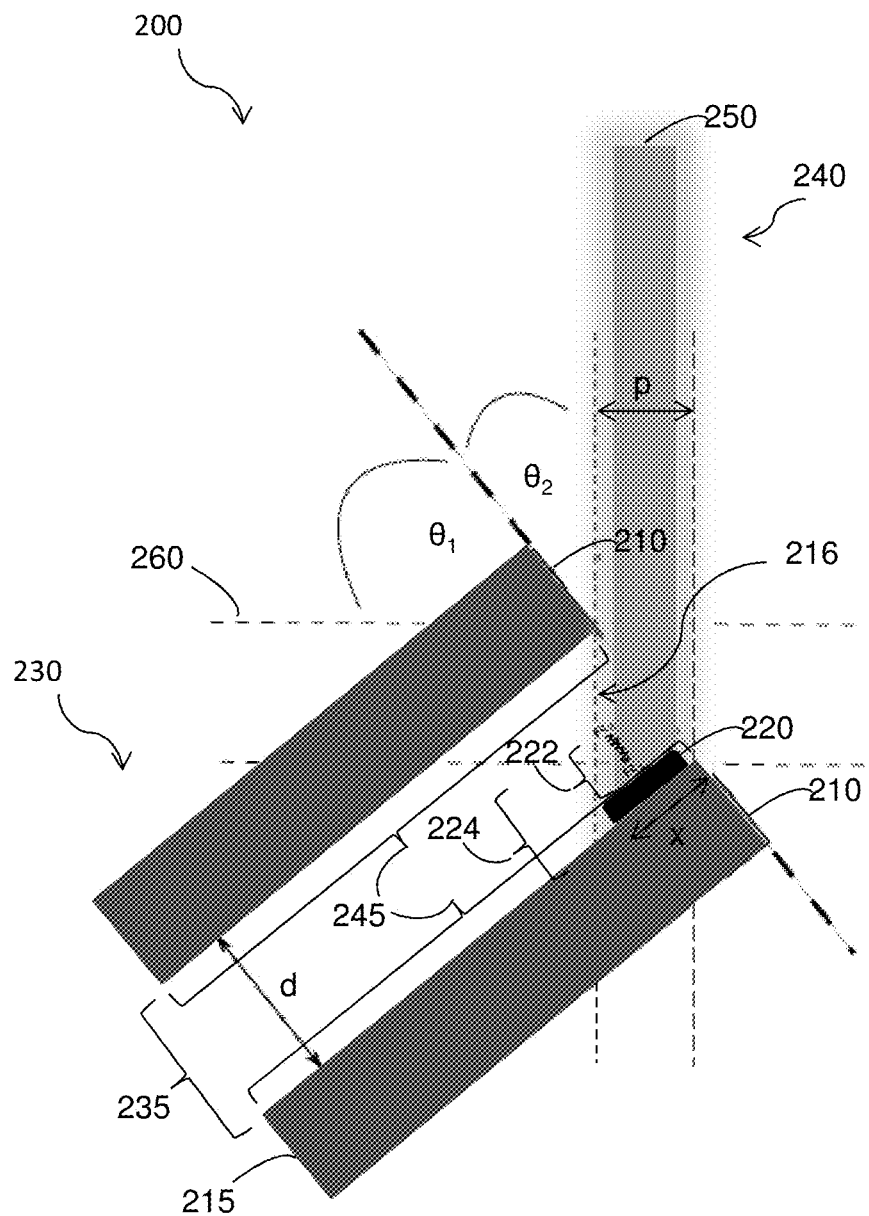
FIG. 2 illustrates a partially cut-away side view of an exemplary embodiment of a method for making a single molecule receptor in a nanopore structure.
Figure 3:
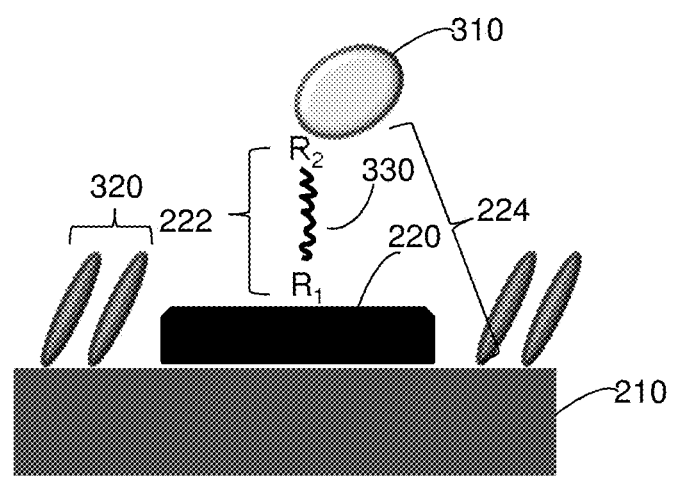
FIG. 3 illustrates a partially cut-away side view of an exemplary embodiment of the single molecule receptor within the nanopore structure of FIG. 2.

Turning now to the figures, FIGS. 1 and 2 are a block diagram and an illustration, respectively, of exemplary embodiments of a method for making a single molecule receptor in a nanopore structure. FIG. 3 illustrates a portion of the nanopore structure with the single molecule receptor, shown in FIG. 2, interacting with an analyte.

Nanopore structures can be fabricated from substrates such as chips, disks, blocks, plates and the like. Such substrates can be made from a variety of materials, including, but not limited to silicon, including silicon oxide, silicon nitride, glass, ceramic, germanium, polymers (e.g., polystyrene), gallium arsenide, or any combination thereof. The substrates can be etched, e.g., chips can be semiconductor chips. The substrate can be a multi-layer substrate. It is not intended for the purpose herein that that any central material in a multi-layer substrate be the same or different than the outer materials. The thickness of the substrate, as well as the thickness of the individual layers within a multi-layer substrate, can generally vary. Thus, the particular thickness of the nanopore substrate is not intended to be limited.

The nanopore substrate can be fabricated using any suitable fabrication process, including but not limited to, chemical vapor deposition (CVD) methods, plasma enhanced chemical vapor deposition (PECVD) methods, lithographic patterning and etching methods, and epitaxial growth processes. Subsequently, the nanochannel within the nanopore can be fabricated through the substrate by any suitable process, including but not limited to, electron beam drilling or ion beam drilling.

FIG. 1 illustrates a block diagram of an exemplary method 100 for making a single molecule receptor in a nanopore structure. In block 110, the method 100 includes depositing a material by a PVD technique onto a selected interior surface of the nanopore structure. In one embodiment, the material forms a patch of material having a diameter of about 1 to about 100 nanometers (nm). In another embodiment, the material forms a patch having a diameter of about 90 nm to about 1,000 nm. In block 120, a surface of the material is functionalized with a chemical compound having at least two functional groups. The method 100 is but an exemplary embodiment. Other embodiments of the method 100 can be used.

FIG. 2 illustrates an exemplary embodiment of a method 200 for making a single molecule receptor 224 in a nanopore structure 230. The method 200 includes depositing by a PVD technique 240 a material 220 onto a selected interior surface of the nanopore structure 230 and then functionalizing a surface of the material 220 with a chemical compound 222. The nanopore structure 230 includes a first surface 210, an opposing second surface 215, and a nanochannel 235 extending from the first surface 210 to the opposing second surface 215 and defining an interior surface 245 of the nanopore structure 230. More specifically, the material 220 is deposited onto the selected interior surface 245 of the nanochannel 235. The nanochannel 235 has a first opening 216 that opens to the first surface 210 and a second opening (not shown) that opens to the second surface 215. The method 200 is but an exemplary embodiment. Other embodiments of the method 200 can be used.

The material 220 can be any material that can be deposited by a PVD technique 240, which will depend on the type of material and surface characteristics of the nanopore structure 230. In one embodiment, the material is a metal, a metal alloy, a semiconductor, an insulator, or any combination thereof. Non-limiting examples of suitable materials include aluminum, platinum, tungsten, gold, silver, nickel, palladium, carbon, cobalt, molybdenum, or any combination thereof.

FIG. 3 illustrates an exemplary embodiment of an enlarged view of a portion of a single molecule receptor 224 in a nanopore structure. Following deposition of the material 220, the material 220 is functionalized with a chemical compound 222. The chemical compound 222 includes at least two functional groups, $R_1$ and $R_2$, which is optionally connected by a linker 330. In another embodiment, functionalizing includes depositing a chemical compound 222 onto the surface of the material 220, and the chemical compound 222 comprises a first functional group $R_1$ that forms a contact product with the material 220, a second functional group $R_2$ that forms a contact product with an analyte 310, and a linker 330 connecting the first functional group $R_1$ to the second functional group $R_2$. The chemical compound 222 can form a self-assembled monolayer (SAM) on the surface, or at least a portion of the surface, of the material 220.

In one embodiment, a nanopore structure comprises a substrate having a first surface and an opposing second surface, a nanochannel extending from the first surface to the opposing second surface and defining an interior surface, a material disposed on a selected area of the interior surface of the nanochannel, and a chemical compound disposed on the material to form a functionalized material. Further, the material has a surface area of about 3 to about 1,000 nm$^2$, and the functionalized material forms the single molecule receptor that binds to an analyte.

At any point following fabrication of the nanopore structure 230, before or after either deposition of the material 220 or functionalization with the chemical compound 222, any SAM can be fabricated on at least a portion of an interior surface 245 of the nanochannel 235. The composition and properties of the SAM generally varies, depends on the composition and properties of the nanopore substrate, and is not intended to be limited. In one embodiment, the SAM comprises silane groups.

The first functional group $R_1$ of the chemical compound 222 can generally vary and is not intended to be limited. Specifically, the first functional group $R_1$ can be any functional group capable of forming a contact product with the material 220. The first functional group $R_1$ can have a specific or non-specific affinity for the material 220. For example, thiols can bind to and form contact products with the surfaces of platinum and gold. In addition, isonitriles form contact products with the surface of platinum. Non-limiting examples of the first functional group $R_1$ are an acyl halide group, an amine group, an amide group, an alcohol group, a carboxylate thiol group, a nitrile group, a phosphate group, a phosphine group, silane group, a sulfate group, a sulfide group, a sulfite group, thiol group, a thiolate group, or any combination thereof.

In one embodiment, the first functional group $R_1$ forms a reversible contact product the material 220. For example, the material 220 can be functionalized with a first chemical compound having one type of first functional group $R_1$, and then the first chemical compound can be removed. Then, the material 220 can be functionalized with a second chemical compound having a first functional group $R_1$ that is different than the initial (first) chemical compound. This process can be repeated, which demonstrates the re-usability of the functionalized nanochannel surface.

The optional linker 330 between the first functional group $R_1$ and second functional group $R_2$ can be any chemical compound, polymer, or biopolymer capable of forming a link between the first and second functional groups $R_1$ and $R_2$. Non-limiting examples of suitable linkers 330 include hydrocarbons, peptides, biopolymers, synthetic polymers (for example polyethylene glycol (PEG)), or any combination thereof The length of the linker 330 can be adjusted to any desired length, which can depend on the identities of the first and second functional groups, $R_1$ and $R_2$ respectively, and the dimensions of the nanochannel 235. Further, the linker 330 can be straight chain or branched.

The second functional group $R_2$ forms the binding site for the analyte 310. The second functional group $R_2$ can be any functional group capable of forming a contact product with a desired analyte 310. Accordingly, the following examples of the second functional group $R_2$ are not intended to be limiting. Suitable examples of the second functional group $R_2$ include small chemical compounds and biochemical compounds, e.g., peptides, proteins, carbohydrates, lipids. Further, any of the above-mentioned chemical compounds for $R_1$ can be used for $R_2$.

The material 220 is deposited onto a selected interior surface 245 of the nanopore 230 by any PVD technique 240 known in the art. PVD techniques 240 are methods for thin film deposition onto a surface. Upon deposition onto the surface, the material forms a thin film, or a patch of the material. The shape, dimensions and composition of the patch generally varies and is not intended to be limited. In one embodiment, the material 220 forms a patch having nanometer dimensions. One layer or multiple layers of one or more materials can be deposited onto a selected interior surface 245 of the nanopore 230 using one or more PVD techniques 240.

Figure 4:
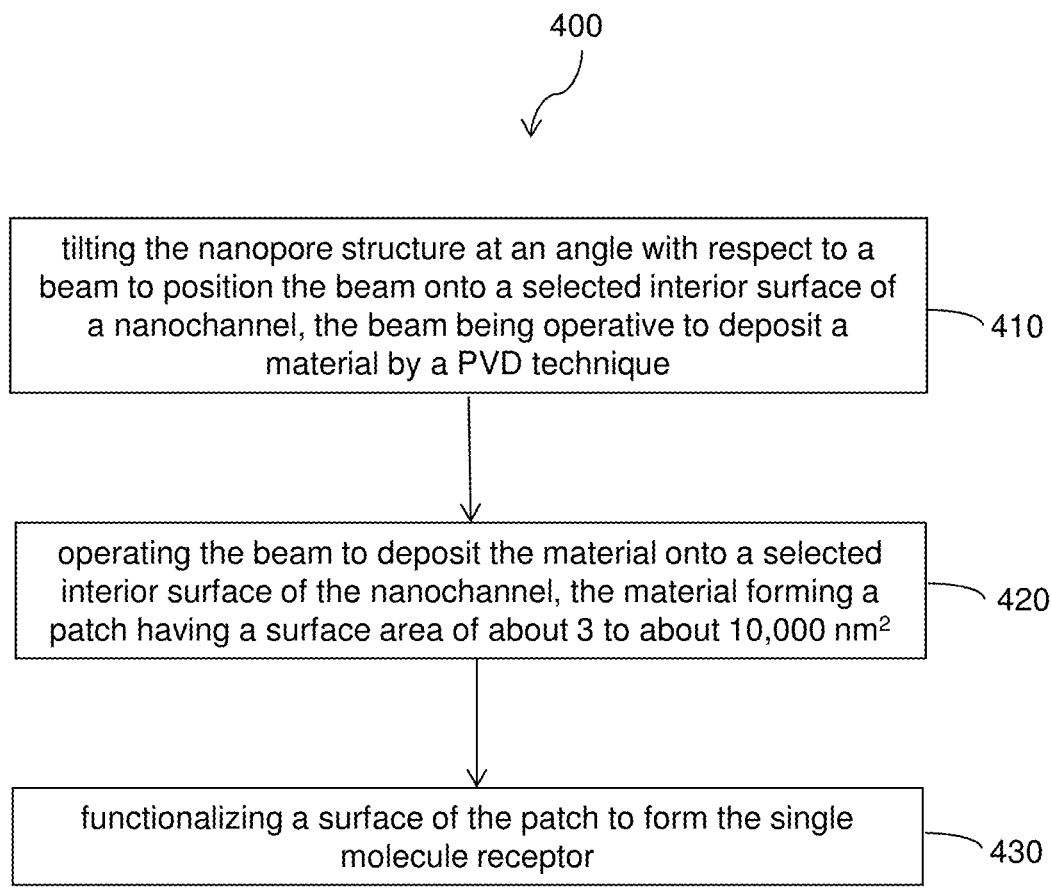
FIG. 4 illustrates a block diagram of an exemplary embodiment of a method for making a single molecule receptor in a nanopore structure.

FIG. 4 illustrates a block diagram of an exemplary method 400 for making a single molecule receptor in a nanopore structure. In block 410, the method 400 includes tilting the nanopore structure at an angle with respect to a beam (see FIG. 2) to position the beam onto a selected interior surface of a nanochannel in the nanopore structure, the beam being operative to deposit a material by a PVD technique. In block 420, the beam is operated to deposit the material onto a selected interior surface of the nanochannel. The material forms a patch having a surface area in a range between about 3 and about 10,000 $nm^2$. In block 430, a surface of the patch is functionalized to form the single molecule receptor.

PVD techniques 240 involve vacuum deposition of a desired material onto a surface by condensation of a vaporized form of the material 220 onto a surface. Non-limiting examples of PVD techniques 240 include pulsed laser deposition/ablation deposition (PLD), sputtering, electron-beam deposition, pulsed electron deposition (PED), or any combination thereof. PVD techniques 240 involve the use of an electron beam or an ion beam to vaporize a target material. Generally, PLD techniques involve use of a high power pulsed laser beam, which is focused inside a vacuum chamber to strike a target of the material that is to be deposited onto a surface. This material is vaporized from the target (in a plasma plume), which deposits the material as a thin film onto a substrate or surface facing or in the vicinity of the target. This process can occur in ultra high vacuum or in the presence of a background gas. Oxygen can be used when depositing oxides to oxygenate the deposited materials.

Generally, sputtering processes involve ejecting material from a target that is a source onto a substrate surface in a vacuum chamber. This effect is caused by the bombardment of the target by ionized gas, which can be an inert gas such as argon.

Generally, electron beam deposition is a process by which a solid material is deposited onto a target material by means of an electron-mediated decomposition of a precursor molecule as a result of electron beam exposure. The electron beam is given off by a tungsten filament under high vacuum. The electron beam induces a dissociation reaction of the introduced vapor plume resulting in a thin layer of solid deposit.

Generally, PED is a process in which a pulsed high power electron beam penetrates a target material, resulting in a rapid evaporation and transformation into the plasma state. The target material in the plasma state is then deposited onto a surface. All solid state materials-metals, semiconductors and insulators, can be deposited as thin films with PED.

In one embodiment, the PVD technique 240 can involve a combined electron beam and focused ion beam (FIB) method, such as a "dual beam" microscope with a metal-deposition add-on. In particular, a microscope that combines high resolution field emission scanning electron microscopy (SEM) and precise focused ion beam (FIB) etch and deposition (for example, a Nova Dual Beam Microscope, Fei Company, Hillsboro, Oreg.), can be used.

Referring again to FIG. 2, to deposit the material 220, the nanopore 230 is tilted with respect to a PVD beam 250. In an exemplary embodiment, the PVD method 240 utilizes a dual beam microscope, and the PVD beam 250 is a combined electron beam and a FIB. The nanopore structure 230 can be disposed onto a microscope stage. Then, the microscope stage, and hence the nanopore structure 230, can be tilted such that the first surface 210 forms an angle $\theta_1$ with respect to a horizontal plane 260. Accordingly, the first surface 210 of the nanopore 230 forms an angle $\theta_2$ ($90°-\theta_1$) with respect to the PVD beam 250. Upon tilting the nanopore 230, the PVD beam 250 is directed through the first opening 216 of the first surface 210 of the nanopore 230 and onto a selected interior surface 245 of the nanochannel 235. Adjusting the tilt parameters, as described below, can be used to fine-tune the precise positioning of the material patch within the nanochannel 235.

The angle $\theta_1$ can be between about 1° and about 52°. In one embodiment, $\theta_1$ can be between about 10° and about 40°. In another embodiment, $\theta_1$ can be between about 20° and about 35°.

Accordingly, the angle $\theta_2$, which equals $90°-\theta_1$, can be between about 38° and about 89°. In one embodiment, $\theta_2$ can be between about 45° and about 75°. In another embodiment, $\theta_2$ can be between about 50° and about 65°.

For a given nanochannel diameter, d, the accessible diameter, p, for the PVD beam 250 equals $\sin(\theta_2)*d$. Further, the position of the material 220 or the distance x from the first surface 210 equals $p/\cos(\theta_2)$. For example, a nanochannel 235 with a diameter of d=20 nm has an access diameter p of about 12 nm and is positioned a distance of about 16 nm (x) from the first surface 210. Accordingly, adjusting the tilt angles $\theta_1$ and $\theta_2$ allows precise positioning within the nanochannel 235, without blocking the first opening 216.

The nanochannel 235 diameter d can be tailored to any application. Accordingly, the following diameters are not intended to be limiting. In one embodiment, the nanochannel diameter d is between about 30 and about 100 nm. In another embodiment, the nanochannel diameter d is between about 10 and about 30 nm. Yet, in another embodiment, the nanochannel diameter d is between about 1 and about 10 nm.

The accessible diameter p, as described above, depends on the nanochannel diameter d and the angle $\theta_2$ ($p=\sin(\theta_2)*d$). Thus, the accessible diameter p can be tailored to any desired application by adjusting the nanochannel diameter d, the angle $\theta_2$, or both. As the accessible diameter p generally varies, the following accessible diameters p are not intended to be limiting. In one embodiment, the accessible diameter p is between about 10 and about 100 nm. In another embodiment, the accessible diameter p is between about 20 and about 80 nm. Yet, in another embodiment, the accessible diameter p is between about 30 and about 60 nm.

After the material 220 is deposited onto the selected interior surface 245 of the nanochannel 235, the material 220 forms a patch positioned a distance x from the from the first surface 210. As mentioned above, the precise position of the patch, or distance x from the first surface 210, depends on the accessible diameter p and $\theta_2$ ($x=p/\cos(\theta_2)=\sin(\theta_2)*d/\cos(\theta_2)=d/\tan(\theta_2)$). Accordingly, the patch distance x can be tailored to any desired application by adjusting the accessible diameter p, the angle $\theta_2$, or both. For example, a nanochannel 235 having a d=20 nm, which is tilted an angle $\theta_2$ of about 41° has an access diameter p of about 12 nm and is positioned a distance of about 16 nm (x) from the first surface 210.

Thus, the following distances, x, from the first surface 210 within the nanochannel 235 are not intended to be limiting. In one embodiment, the distance x from the first surface 210 is between about 1 and about 50 nm. In another embodiment, the distance x from the first surface 210 is between about 10 and about 40 nm. Yet, in another embodiment, the distance x from the first surface 210 is between about 15 and about 35 nm.

The size of the patch, or the patch diameter (not shown), can be variable and can be adjusted on the instrumentation used to deposit the material. Thus, the following patch diameters are not intended to be limiting. In one embodiment, the patch diameter is between about 1 and about 100 nm. In another embodiment, the patch diameter is between about 10 and about 80 nm. Yet, in another embodiment, the patch diameter is between about 20 and about 60 nm.

The material 220 can be deposited onto the selected interior surface 245 of the nanochannel 235 in one or more layers, which can include one or more materials. The thickness of the patch of at least one material 220 can have any size, thickness, or shape. Non-limiting examples of shapes for the patch of material 220 include a circle, ring, oval, square, triangle, rectangle, ring, or any combination thereof. In one embodiment, the patch is in the shape of a ring encircling the inner circumference of the nanochannel 235.

The patch of material 220 can have any thickness, which again can be tailored to the desired application. Thus, the following patch thicknesses are not intended to be limiting. In one embodiment, the patch thickness is between about 0.5 and about 10 nm, which depends on the material. In another embodiment, the patch thickness is between about 2 and about 8 nm. Yet, in another embodiment, the patch thickness is between about 4 and about 6 nm.

Furthermore, the surface area of the patch of material 220 can be adjusted to the application. Accordingly, the following surface areas are not intended to be limiting. In one embodiment, the patch of material 220 has a surface area between about 3 and about 1,000 nm$^2$. In another embodiment, the patch of material 220 has a surface area between about 100 and about 800 nm$^2$. Yet, in another embodiment, the patch has a surface area between about 250 and about 600 nm$^2$.

Figure 5:
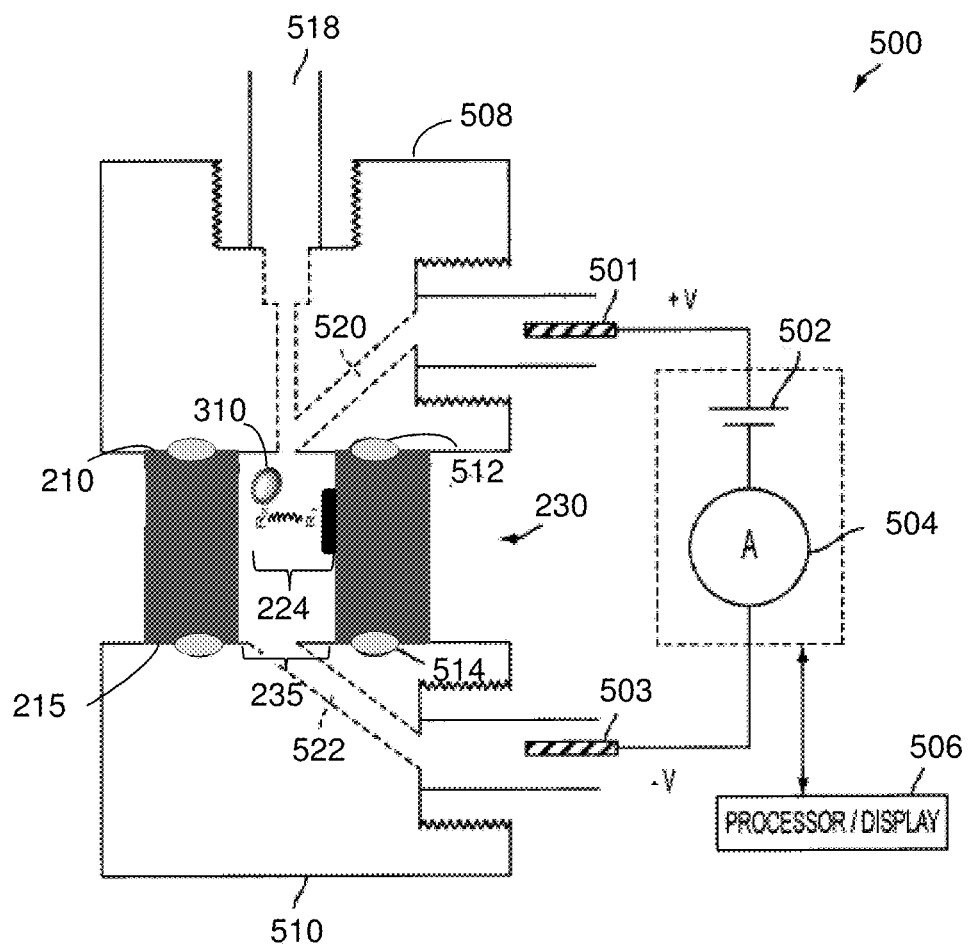
FIG. 5 illustrates a partially cut-away side view of a method for using the single molecule receptor within the nanopore structure of FIGS. 2 and 3.

FIG. 5 illustrates an exemplary embodiment of a method 500 for using a nanopore structure 230 having a single molecule binding site 224. During analysis of an analyte 310, the nanopore should allow for a sufficiently large ionic current under an applied electric field to provide for adequate measurement of current fluctuations. Current fluctuations are induced by binding and un-binding of an analyte 310 to the single molecule receptor 224 and/or translocation of the analyte 310 through the nanochannel 235 of the nanopore structure 230. Thus, when a single molecule of an analyte 310 binds to the single molecule receptor 224, current fluctuations can be measured. These current fluctuations provide chemical and biochemical information about the analyte 310.

The nanopore structure 230 defines a fluidic cell having a first cell portion 508 and a second cell portion 510. In particular, the nanopore structure 230 is disposed between the first cell portion 508 and the second cell portion 510. The nanopore structure 230 includes a patch of a functionalized material, which forms the single molecule receptor 224, disposed onto a selected area of the interior surface 245 of the nanochanne 1235 of the nanopore structure 230.

A first seal portion 512 is sealingly engaged between the first cell portion 508 and the first surface 210 of the nanopore structure 230. A second seal portion 514 is sealingly engaged between the second surface 215 of the nanopore structure 230 and the second cell portion 510. The first and second seal portions 512 and 514 can be o-ring gaskets made of, for example, silicon. The first cell portion 508 defines a first port 518 and a second port 520 that are in fluid communication with the nanochannel 235 within the nanopore structure 230. The second cell portion 510 defines a third port 522 and a fourth port (not shown) that are in fluid communication with the nanochannel 235 within the nanopore structure 230.

A voltage source 502 is shown arranged with electrodes 501 and 503 disposed in the second port 520 and the third port 522. A current sensing device 504 is operative to detect changes in current between the electrodes 501 and 503. The current sensing device 504 can be controlled by a personal computer through operative software. The current has a current path defined by the nanochannel 235 within the nanopore structure 230.

Prior to analysis of the analyte 310, buffered salt solutions are first introduced into the nanochannel 235. The buffered salt solutions are introduced via the first port 518 and the third port 522. The buffered salt solution can be flushed from the nanochannel 235 via the second port 520 and the fourth port (not shown). However, in alternate embodiments, the roles of the ports may be reversed. The electrodes 501 and 503 are communicative with the buffered salt solutions. The current has a current path defined by nanochannel 235, and the current is affected by the analyte 310 binding to the single molecule receptor 224 and/or passing through the nanochannel 235. Upon introduction of an analyte 310 to the nanochannel 235, the analyte 310 will bind to, or form a contact product with, the single molecule receptor 224. The result is a detectable change in ionic current output.

The buffered salt solutions generally vary and depend on the particular analyte and application. The buffered salt solutions can include any electrolytes, ions, buffers, or components desired.

The ionic current in the current path is measured by the current sensing device 504 that may be connected to a processing and display device 506 that may include, for example, a computer processor and display operative to process the sensed current values and output a logical result to a user on the display. As mentioned above, the current is affected by analytes 310 passing through and binding to the single molecule receptor 224. Thus, the analyte 310 may be introduced into nanochannel 235 via the first port 518 in any buffer, solution, or solvent desired. The method 500 is but an exemplary embodiment. Other embodiments of the method 500 can be used.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. A nanopore structure comprising a single molecule receptor, the nanopore structure comprising:
    a substrate having a first surface and an opposing second surface;
    a nanochannel extending from the first surface to the opposing second surface and defining an interior surface;
    a raised patch of a material disposed onto a selected area of the interior surface of the nanochannel, wherein the raised patch does not fully encompass the circumference of the nanochannel, the raised patch material having a surface area of about 3 to about 10,000 $nm^2$ and extending from the selected area of the interior surface to the nanochannel's opening; and
    a chemical compound disposed onto the material to form a functionalized material that forms the single molecule receptor;
    wherein the single molecule receptor is a binding site with nanometer dimensions that binds to only a single molecule of an analyte in a complex sample.

2. The nanopore structure of claim 1, wherein the material is aluminum, platinum, tungsten, gold, silver, nickel, palladium, carbon, cobalt, or any combination thereof.

3. The nanopore structure of claim 1, wherein the chemical compound comprises a first functional group that forms a contact product with the material, a second functional group that forms a contact product with the analyte, and a linker connecting the first functional group to the second functional group.

4. The nanopore structure of claim 3, wherein the first functional group is a an acyl halide group, an amine group, an amide group, an alcohol group, a carboxylate thiol group, a nitrile group, a phosphate group, a phosphine group, silane group, a sulfate group, a sulfide group, a sulfite group, thiol group, a thiolate group, or any combination thereof.

5. The nanopore structure of claim 3, wherein the linker is a hydrocarbon, a peptide, a synthetic polymer, or any combination thereof.

6. The nanopore structure of claim 1, wherein the nanochannel diameter is about 30 to about 100 nm.

7. A nanopore structure comprising a single molecule receptor, the nanopore structure comprising:
    a substrate having a first surface and an opposing second surface;
    a nanochannel extending from the first surface to the opposing second surface and defining an interior surface;
    a raised patch of a material disposed onto a selected area of the interior surface of the nanochannel, wherein the raised patch does not fully encompass the circumference of the nanochannel, the raised patch having a diameter of about 1 to about 100 nm and a thickness of about 0.5 to about 10 nm and extending from the selected area of the interior surface to the nanochannel's opening; and
    a chemical compound disposed onto the material to form a functionalized material that forms the single molecule receptor;
    wherein the single molecule receptor is a binding site that binds to a single molecule of an analyte in a single binding event.

* * * * *